United States Patent
Hansson

(10) Patent No.: US 7,179,246 B2
(45) Date of Patent: Feb. 20, 2007

(54) OPENING ARRANGEMENT FOR SINGLE-WRAPPED ABSORBENT ARTICLES

(75) Inventor: Roy Hansson, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 569 days.

(21) Appl. No.: 10/617,396

(22) Filed: Jul. 11, 2003

(65) Prior Publication Data
US 2004/0064122 A1    Apr. 1, 2004

Related U.S. Application Data

(60) Provisional application No. 60/394,877, filed on Jul. 11, 2002.

(51) Int. Cl.
*A61F 13/15* (2006.01)
*A61B 17/06* (2006.01)

(52) U.S. Cl. ............ 604/385.02; 604/385.13; 206/440; 206/503

(58) Field of Classification Search ........... 604/385.02, 604/385.01, 385.13; 206/440, 714, 204, 206/581, 813, 554, 752, 503, 750
See application file for complete search history.

(56) References Cited

U.S. PATENT DOCUMENTS

| 4,564,108 | A | 1/1986 | Widlund et al. |
| 4,674,634 | A * | 6/1987 | Wilson ............ 206/554 |
| 2002/0056655 | A1* | 5/2002 | Cottingham et al. ..... 206/440 |
| 2002/0084203 | A1 | 7/2002 | Cottingham |

OTHER PUBLICATIONS

International Search Report issued in a corresponding patent application.

* cited by examiner

*Primary Examiner*—Jacqueline F. Stephens
(74) *Attorney, Agent, or Firm*—Buchanan Ingersoll & Rooney PC

(57) ABSTRACT

A stack of absorbent articles includes at least a first absorbent article and a second absorbent article adjacent in the stack, each article being individually wrapped in a wrapping cover with a container part and a lid part releasably attached to the outside of the container part. The lid part on the second absorbent article is attached to the wrapping cover of the first absorbent article by a releasable attachment which is stronger than the attachment between the lid part and the container part on the wrapping cover of the second absorbent article.

8 Claims, 3 Drawing Sheets

OPENING ARRANGEMENT FOR SINGLE-WRAPPED ABSORBENT ARTICLES

CROSS-REFERENCE TO RELATED APPLICATIONS

The present application claims the benefit of U.S. Provisional Application No. 60/394,877, filed in the United States on Jul. 11, 2002, the entire contents of which are hereby incorporated herein by reference.

BACKGROUND OF THE APPLICATION

1. Technical Field

The present invention relates to a stack of absorbent articles for absorption of body fluids, each article being individually wrapped.

2. Background Art

Absorbent articles for personal hygiene, especially those articles which are intended to be worn inside ordinary briefs and are in this connection fitted in the briefs by the user personally, are often single-wrapped. Single wrapping means that each absorbent article is packed in a wrapping cover. In this way, it is simple for the user, in an easy and hygienic manner, to carry one or more absorbent articles, for example in a handbag. Examples of the type of absorbent article concerned are sanitary towels, panty liners and incontinence pads for people with mild to moderate incontinence.

The most common way of single-wrapping absorbent articles is by folding them together into a smaller size, after which they are packed in a thin wrapping cover made of plastic or paper. Such a wrapping cover often consists of a rectangular piece of material, which has been folded twice in its transverse direction and subsequently joined together along its side edges so that a bag-like container for the absorbent article is formed, and also a lid part which can close the container. In the closed state of the wrapping cover, the lid part is frequently fastened in the edge joins on the outside of the container part by releasable joins, such as breakable welds or releasable glue. There can also be further sealing between the lid part and the container part along the end edge of the lid part. Such sealing can be in the form of, for example, releasable glue, hook and loop means, tape flaps or the like. If the sealing means allows resealing, it can also be used for closing the wrapping cover if it is used for wrapping up an absorbent article after use.

It has been found, however, that the known single wrappings can be difficult to open. As the wrapping material is thin and flexible, the lid part will come to lie close to the outside of the container part. This problem is accentuated by the fact that absorbent articles of the type concerned here are packed with a large number of individually wrapped articles in a larger outer packing. In this connection, the articles are pressed together with a fair degree of force, the wrapping covers also being subjected to being pressed together, which of course means that the lid part of the wrapping cover is pressed against the outside of the container part. Owing to the strong compression of the wrapping material and the fact that the wrapping material is usually very thin and flexible, it has become apparent that many users find it difficult to grip the edge of the lid part so that the wrapping cover can be opened. It can be very difficult both to discern the edge visually and to feel where it is with the fingers. This is clearly a particular problem for people with impaired vision or with limited manual dexterity. As the occurrence of incontinence increases with increasing age, as do vision problems and problems of poor mobility and/or feeling in the hands, handling of the known single wrappings is therefore a common and particularly irritating problem especially for older users of absorbent articles.

OBJECTS AND SUMMARY

One object of the present invention is therefore to provide a wrapping cover for a single-wrapped absorbent article, which wrapping cover is improved with regard to openability.

In accordance with the invention, a stack of wrapped absorbent articles of the type referred to in the introduction has therefore been produced. According to one embodiment, each wrapping cover has a container part with an inside and an outside and an opening for removal of the absorbent article, and a lid part which has an open state and a closed state. The lid part, in the closed state, closes the opening of the container part and is releasably attached to the outside of the container part. The lid part on the second absorbent article is attached to the wrapping cover of the adjacent first absorbent article by a releasable attachment which is stronger than the attachment between the lid part and the container part on the wrapping cover of the second absorbent article. By virtue of this arrangement, the first wrapping cover will be opened automatically when the first wrapping cover is detached from the second wrapping cover.

Calling the absorbent articles and the wrapping covers a first and a second absorbent article or wrapping cover is not intended to define the position of the articles and the wrapping covers in the stack. Instead, the intention is to distinguish between two adjacent wrapping covers. The first and second absorbent articles can therefore be positioned anywhere in a stack, that is to say at one or both end(s), or within the stack. This means that the stack can comprise further absorbent articles, which can be attached to one another in the manner according to the invention, or can be free of such connections. A stack of absorbent articles can furthermore consist of a number of part stacks which, within each part stack of two or more absorbent articles, can have at least two absorbent articles with connections which allow automatic opening of the wrapping covers enclosing the absorbent articles.

According to one embodiment of the invention, the lid part on the second wrapping cover is attached to the container part of the first wrapping cover.

According to another embodiment of the invention, the lid part on the second wrapping cover is attached to the lid part of the first wrapping cover.

A wrapping cover according to one embodiment of the invention is advantageously formed by a rectangular piece of material with a longitudinal direction and a transverse direction and having two side edges extending in the longitudinal direction, and two end edges extending in the transverse direction. The wrapping cover also has two fold lines arranged in the transverse direction which divide the wrapping cover into a first end panel, a second end panel and a central panel, the first end panel and the central panel being interconnected in side edge joins along the side edges and thus forming the container part of the wrapping cover, and the second end panel forming the lid part of the wrapping cover. In such an embodiment, the lid part can advantageously be fastened in the side edge joins by a tear-open fastening. Examples of such tear-open fastenings are welds which have been embossed and/or release-agent-treated. It is also possible to use releasable adhesive joins.

It is also advantageous if the fastening between the container part and the lid part on each wrapping cover comprises a resealable sealing means for the lid part of the wrapping cover. Such a resealable sealing means can be used for closing the wrapping around a used absorbent article.

A stack of absorbent articles according to the invention can be placed in an outer packing having an inside and an outside. In order to facilitate opening of the first wrapping cover as well, the lid part of the latter can be attached to the inside of the outer packing by a releasable attachment which is stronger than the attachment between the lid part and the container part on the wrapping cover of the first absorbent article.

BRIEF DESCRIPTION OF THE DRAWINGS

The embodiments of the invention will be described in greater detail below with reference to the figures which are shown in the accompanying drawings and in which.

DETAILED DESCRIPTION OF THE PREFERRED EMBODIMENTS

Figure 1:
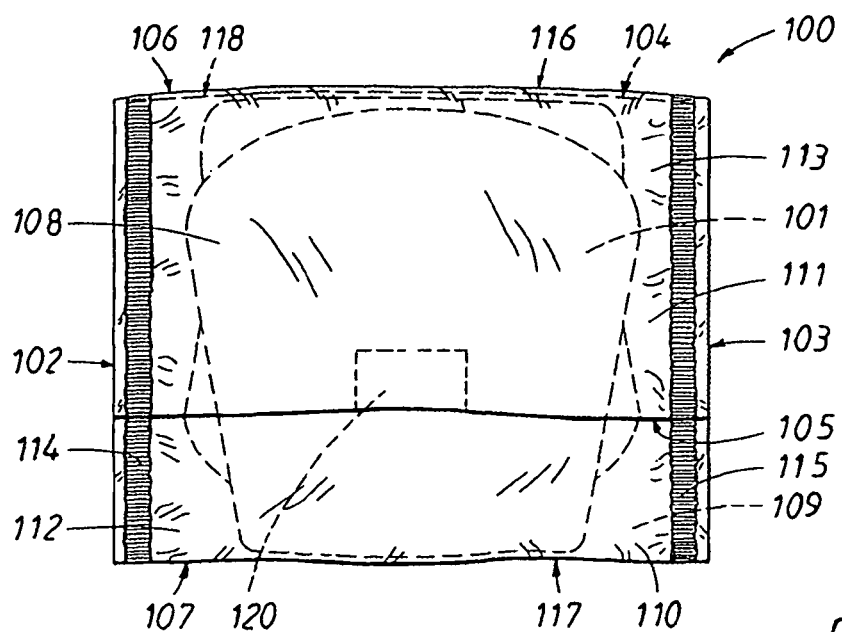
FIG. 1 shows a sanitary towel enclosed in a wrapping cover.

FIG. 1 shows a plan view of a wrapping cover 100 in which a sanitary towel 101 is wrapped according to one embodiment of the present invention. The wrapping cover 100 is formed by a piece of material 113 of rectangular shape, the piece of material 113 having two side edges 102, 103 which also constitute side edges 102, 103 of the wrapping cover, and two end edges 104, 105. The wrapping cover is folded together along a first fold line 106 and a second fold line 107 so that three panels 108, 109, 110 are formed, a first end panel 108 constituting the lid part 111 of the wrapping cover, and a second end panel 110 and the central panel 109 located between the end panels together forming the container part 112 of the wrapping cover. The container part 112 is closed along the side edges 102, 103 of the wrapping cover 100 by edge joins 114, 115. In the example shown, the edge joins are embossed welds, but it is of course possible to produce edge joins in another way, for example using glue. In the illustrative embodiment shown, the lid part 111 also is fastened in the edge joins, which means that the wrapping cover as it is shown in FIG. 1 is in a closed state. It is advantageous if the lid part 111 can be freed simply from the container part along the edge joins 114, 115 without the wrapping material being torn apart. This can be achieved by making the edge joins 114, 115 openable at least between the lid part 111 and the container part 112. Alternatively, the lid part can be provided with means which make controlled opening/tearing open of the lid part 111 possible. Such a means may be, for example, perforations arranged inside the edge joins on the lid part 111. For some embodiments, it may be suitable for the edge joins 114, 115 to be completely openable, for example if it is desirable for it to be possible to open out the wrapping cover entirely when the sanitary towel 101 is to be removed from the wrapping cover.

As mentioned above, the wrapping cover 100 has two side edges 102, 103 in its folded and joined together state. The wrapping cover also has a first end edge 116 and a second end edge 117, which edges extend at right angles to the side edges 102, 103 and coincide with the first and second fold lines 106, 107 of the wrapping cover. The first end edge 116 also constitutes an inner edge of the lid part, while the outer edge 105 of the lid part 111 coincides with one end edge 105 of the piece of material 113 and is located part of the way down on the second end panel 110, on the outside of the container part 112. The wrapping cover 100 also has an opening 118 which is located between the second end panel 110 and the central panel 109 at the first end edge 116 of the wrapping cover, inside the first fold line 106 in the piece of material 113. The opening makes it possible for the sanitary towel 101, after opening of the wrapping cover, to be removed from the container part 112.

The lid part is also attached to the container part by a sealing means 120 which is arranged in the form of a glued surface at the outer edge 105 of the lid part 111, centrally between the side edges 102, 103 of the wrapping cover. The sealing means 120 can be detached from the container part 112, for opening the wrapping cover 100. It is advantageous if the sealing means is resealable. In this way, it is possible to use the wrapping cover as a disposal wrapper for a used sanitary towel. It is of course not necessary for the invention that the sealing means is of an adhesive type or that it has the shape and size shown. It is therefore possible to use various types of mechanical sealing means, such as hook and loop means, press-studs or the like. It is likewise possible to arrange the sealing means along the entire outer edge 105 of the lid part 111, as it is to arrange the sealing means 120 part of the way in on the lid part 111. It is also possible to arrange a number of sealing means between the lid part and the container part. If the fastening of the lid part 111 in the edge joins 114, 115 is deemed to afford sufficient closing of the wrapping cover, the separate sealing means can be omitted completely. In a corresponding way, the sealing means 120 can of course replace the fastening of the lid part 111 in the edge joins.

The sanitary towel 101 wrapped in the wrapping cover 100 can of course be of any type. It is clearly not necessary either for the wrapped absorbent article to be just a sanitary towel, but other types of absorbent article such as panty liners and incontinence pads can alternatively be wrapped in the wrapping cover shown in FIG. 1. The exact design of an absorbent article wrapped in a wrapping cover according to the invention is therefore not critical for the invention, but a number of different variants and designs of absorbent article are therefore conceivable. However, the invention is applicable mainly, but not exclusively, to absorbent articles which are so small that they allow single wrapping or can be folded together into a size suitable for single wrapping and can thus be stored and transported easily and discreetly in, for example, a pocket, a toilet bag or a handbag.

Figure 2:
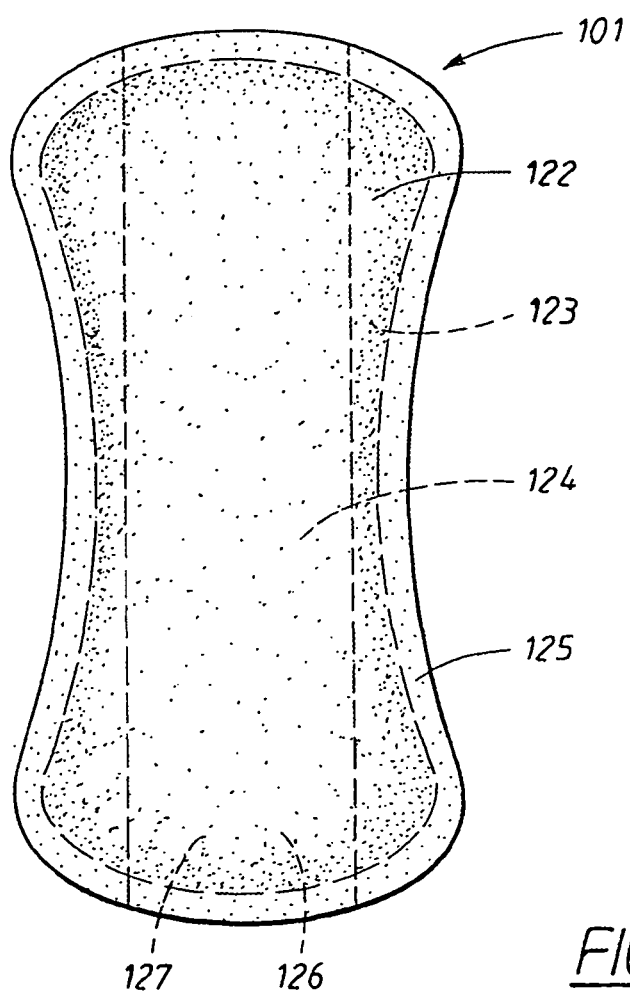
FIG. 2 shows a plan view of a sanitary towel.

FIG. 2 shows a plan view of the sanitary towel enclosed in the wrapping cover 100 in FIGS. 1 and 2, seen from the side which is intended to face the wearer during use. The sanitary towel 101 in FIG. 2 has a conventional construction, with a liquid-permeable covering layer 122, a liquid-impermeable covering layer 123 and an absorbent body 124 enclosed between the covering layers 122, 123. The covering layers 122, 123 are interconnected, for example by gluing or welding, the join between the covering layers forming a covering edge 125 which extends around the entire periphery of the absorbent body 124. Alternative embodiments of absorbent article, in which a liquid barrier layer is arranged on that surface of the absorbent body which faces away from the wearer during use and inside a liquid-permeable outer covering layer which surrounds the whole absorbent body are also known and fall within the scope of the invention.

Common liquid-permeable covering layers are perforated and unperforated nonwoven materials, net materials, liquid-permeable foam, perforated plastic films or the like. Combinations and laminates of materials can also be used. Thin plastic film is commonly used as the liquid-impermeable covering layer, but it is also known to form a liquid barrier by means of a coating of wax or glue. Use has also been made of impermeable foamed materials and nonwoven materials with a greater or lesser degree of liquid-impermeability.

The absorbent body 124 in an absorbent article such as a sanitary towel or the like is often constructed from one or more layers of absorbent material, such as cellulose fluff pulp, tissue, fibre wadding or the like. It is also common to use what are known as superabsorbent materials, which are polymers which are available in the form of particles, flakes, fibres, granules or films and can absorb liquid corresponding to several times their own weight while forming a liquid-containing gel.

The sanitary towel in FIG. 2 can also comprise components which have not been drawn, such as liquid-receiving layers, liquid-transport layers, stiffening elements, reinforcing means, compressions, elastic means, side barriers etc. Sanitary towels and panty liners which are expected to receive very small quantities of liquid do not have to be provided with a special absorbent body, but a surface layer which provides a certain absorption capacity may be sufficient.

In order to be capable of being fastened in a pair of briefs, the sanitary towel 101 is provided with an attachment means in the form of an adhesive surface 126 arranged on the liquid-impermeable covering layer 123. Before use, the adhesive surface 126 is covered by a protective layer 127, for example of siliconized paper. Alternatively, the wrapping cover 100 can of course be used as a protective layer. In this connection, it is usual for the sanitary towel to be placed on the wrapping cover 100 before the latter is folded together to form a wrapping. In such an embodiment, therefore, the sanitary towel and the wrapping cover are folded together simultaneously and not individually.

The adhesive surface can be an overall adhesive coating or can be arranged in a pattern, usually of stripes or dots. A number of adhesive surfaces can be arranged on the liquid-impermeable covering layer and can then be covered by a common protective layer or a number of separate protective layers. It is clearly possible to omit the attachment means, or to use other types of attachment means, such as hook and loop surfaces, press-studs, friction coatings etc. An especially common type of combined attachment arrangement and leakage barrier is attachment flaps which are arranged along the side edges of the absorbent article and, during use, are folded around the crotch portion of the briefs of the user and attached on the outside of the briefs. Such attachment flaps are often used in combination with attachment glue on the underside of the absorbent article.

FIGS. 3–6 show diagrammatically various embodiments of stacks of articles in accordance with the invention. For the sake of simplicity, and in order to clarify the wrapping principle, the wrapped articles have been shown as homogeneous bodies, without folds and different layers. Seals between the lid part and the container part on the individual wrapping covers have not been drawn either, but can be present, as described in connection with FIG. 1.

Figure 3:
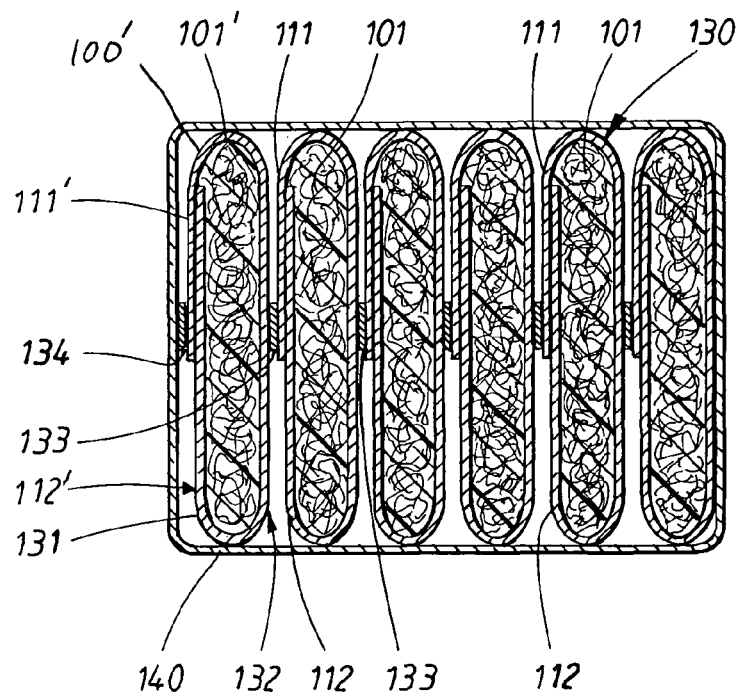
FIG. 3 shows a diagrammatic section through a stack of wrapping covers according to a first embodiment of the invention, enclosed in an outer packing.

FIG. 3 shows a stack 130 of a number of absorbent articles 101, each wrapped in a wrapping cover 100 of the type described in connection with FIG. 1. The wrapping covers 100 are all oriented in the same way in the stack 130 and have a front side 131 and a rear side 132, the lid part 111 on each wrapping cover being arranged on the front side 131, while the rear side 132 consists entirely of the central panel 109 of the wrapping cover 100. The wrapping covers 100 are interconnected in such a way that the lid part 111 on one wrapping cover is connected to the rear side 132 of the wrapping cover 100 immediately in front. The connection is made by means of connections 133, which may be glue, welds or the like. The strength of the connection between the various wrapping covers 100 is greater than the strength of the connection between the lid part 111 and the container part 112 of each wrapping cover. This means that the connections 133 between the wrapping covers are to be stronger than the combined connections between the lid part 111 and the container part 112. As described above, the sealing connection between each lid part 111 and the container part 112 can comprise edge seals and/or separate sealing means.

By virtue of the fact that the connections 133 between the wrapping covers 100 are stronger than the connections between the lid part 111 and the container part 112 on each wrapping cover 100, the wrapping covers will be opened automatically when the wrapping covers are pulled apart.

As shown in FIG. 3, the whole stack 130 of absorbent articles 101 is placed in an outer packing 140. The outer packing shown has been indicated only diagrammatically and can of course comprise joins and be designed in a corresponding manner to the individual wrapping covers and therefore have a container part and a lid part. The design of the outer packing is not critical for the invention, but any packing type suitable for the purpose can be used. An outer packing 140 for single-wrapped absorbent articles usually consists of a plastic bag or a carton and often accommodates one or more stacks of absorbent articles. Single-wrapped absorbent articles are usually supplied in an outer packing, which serves as protection during transport and a storage packing before the sale of the absorbent articles. The outer packing is then used as a stock from which individual wrapped articles can be removed as they are required.

The wrapping cover 100' which has its lid part 111' facing the outer packing 140 is attached by the lid part 111' to the inside of the outer packing 140 by a connection 134 of the same type as the connections 133 between the wrapping covers 100. In this way, it is possible to achieve automatic opening of this wrapping cover 100' as well, which is normally removed from the outer packing 140 last.

Figure 4:
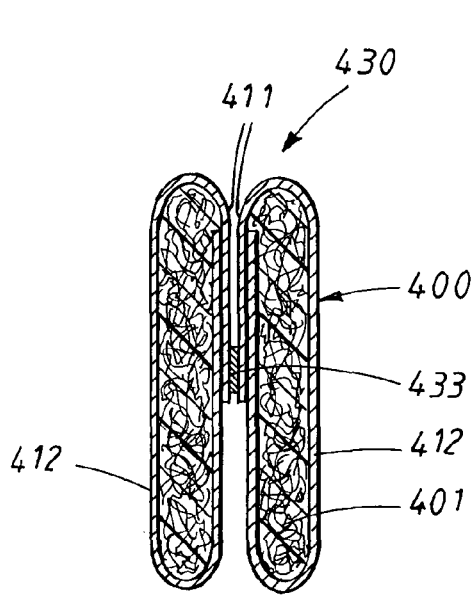
FIG. 4 shows a diagrammatic section through a stack of wrapping covers according to a second embodiment of the invention.

FIG. 4 shows a stack 430 consisting of two wrapping covers 400 which are put together with their lid parts 411 facing one another and with a connection 433 arranged between the lid parts 411. The connection 433 is, in the same way as described in connection with FIG. 3, adapted so that it withstands the forces required in order to free each lid part 411 from the container part 412 but can be freed when a slightly greater pulling force is applied. When the wrapping covers 400 are pulled apart, the two wrapping covers 400 will therefore be opened simultaneously by virtue of the lid parts 411 being freed from their respective container parts 412. An advantage of the embodiment shown in FIG. 4 is that, when the wrapping covers are placed in an outer packing, automatic opening of all wrappings is achieved, without a wrapping cover having to be attached to the outer packing. A small disadvantage, however, is that it is not possible to open only one wrapping cover, but both covers in a pair are opened simultaneously.

The solution shown in FIG. 4 can also be applied to two oppositely arranged stacks of the type shown in FIG. 3. Individual wrapping covers can then be gradually removed from the ends of the stacks until only the final pair of wrapping covers remains. This last pair then has the appearance shown in FIG. 4. A stack according to the invention can of course also comprise two or more pairs of wrapping covers 400 of the type shown in FIG. 4.

Figure 5:
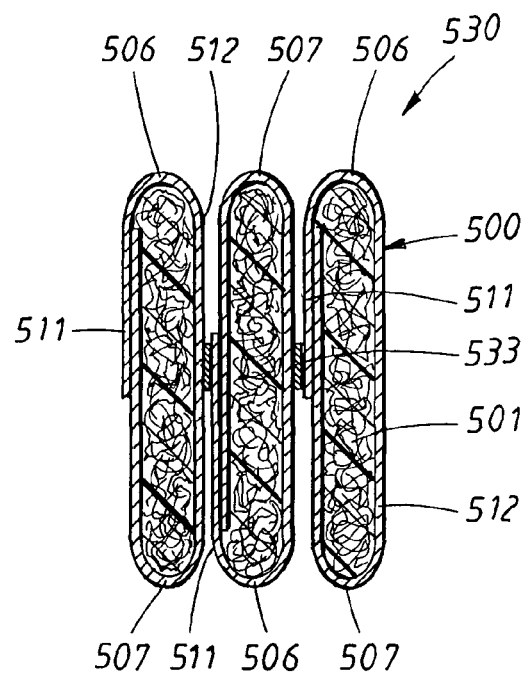
FIG. 5 shows a diagrammatic section through a stack of wrapping covers according to a third embodiment of the invention.

FIG. 5 shows a stack 530 of single-wrapped absorbent articles 501 which corresponds in functional terms to the stack 130 shown in FIG. 3. However, the stack 530 in FIG. 5 differs from that in FIG. 3 in that the wrapping covers 500 are oriented with their lid parts 511 rotated through 180° in relation to one another. Such an embodiment is advantageous as it produces a symmetrical stack, with essentially the same height at the sides formed by the folded edges 506, 507 of the wrapping covers 500.

Figure 6:
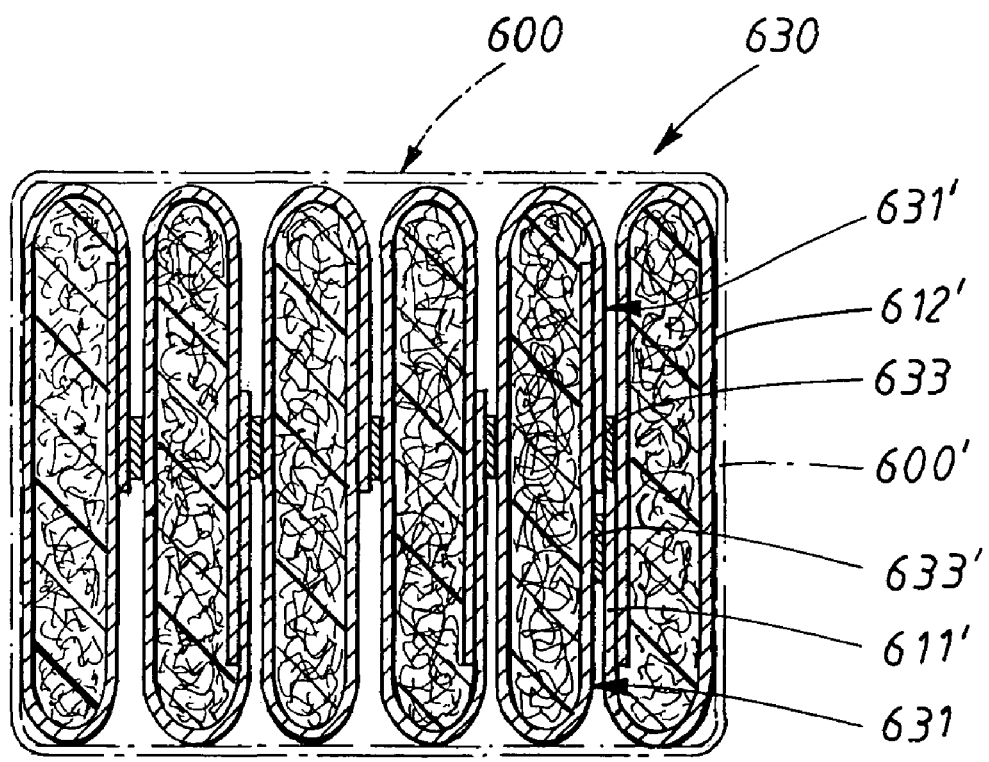
FIG. 6 shows a diagrammatic section through a stack of wrapping covers according to a fourth embodiment of the invention.

FIG. 6 shows an alternative way of bringing about automatic opening of all the wrapping covers 600 in a stack 630 of absorbent articles 601. Instead of, as in the illustrative embodiment shown in FIG. 3, attaching the last wrapping cover 600' to an outer packing, the last wrapping cover 600' is turned with the front side 631', that is to say with the lid part 611', towards the front side 631 of the immediately adjacent wrapping cover 600. In the example shown in FIG. 6, the last wrapping cover 600' has been rotated in relation to the next last wrapping cover, so that the lid part 611' on the last wrapping cover 600' is attached by a connection 633' to the container part 612 on the front side 631 of the next last wrapping cover 600. Conversely, the lid part 611 on the next last wrapping cover 600 is attached by a connection 633 to the container part 612' on the front side 631' of the last wrapping cover 600'. In the rest of the stack 630 as well, the wrapping covers 600 are arranged with the lid parts 611 oriented in alternating directions in the same way as in FIG. 5. It is also possible, however, to apply the opening principle shown in FIG. 6 to a stack of the type shown in FIG. 3. The last two wrapping covers can then be turned in relation to one another in the way shown in FIG. 4. Alternatively, they can of course be rotated as in FIG. 6, even if all the other wrapping covers included in the stack are turned by 180° in relation to one another.

All the stacks of single-wrapped absorbent articles described above can of course be placed in an outer packing, as described in connection with FIG. 3.

The invention is not limited to the illustrative embodiments described above, but a number of modifications are possible within the scope of the patent claims below.

What is claimed is:

1. A stack of absorbent articles for absorption of body fluids and comprising at least two absorbent articles constituting a first absorbent article and a second absorbent article adjacent in the stack, each article being individually wrapped in a wrapping cover comprising a container part with an inside and an outside and an opening for removal of the absorbent article, and a lid part which has an open state and a closed state, the lid part, in the closed state, closing the opening of the container part and being releasably attached to the outside of the container part, wherein the lid part on the second absorbent article is attached to the wrapping cover of the first absorbent article by a releasable attachment which is stronger than the attachment between the lid part and the container part on the wrapping cover of the second absorbent article.

2. The stack of absorbent articles according to claim 1, in which the lid part on the second wrapping cover is attached to the container part of the first wrapping cover.

3. The stack of absorbent articles according to claim 1, in which the lid part on the second wrapping cover is attached to the lid part of the first wrapping cover.

4. The stack of absorbent articles according to claim 1, in which each wrapping cover is formed by a rectangular piece of material with a longitudinal direction and a transverse direction and having two side edges extending in the longitudinal direction, and two end edges extending in the transverse direction, and in which the wrapping cover also has two fold lines arranged in the transverse direction which divide the wrapping cover into a first end panel, a second end panel and a central panel, the first end panel and the central panel being interconnected in side edge joins along the side edges and thus forming the container part of the wrapping cover, and the second end panel forming the lid part of the wrapping cover.

5. The stack of absorbent articles according to claim 4, in which the lid part is fastened in the side edge joins by a breakable seal.

6. The stack of absorbent articles according to claim 5, in which the breakable seal consists of a tear-open welded join.

7. The stack of absorbent articles according to claim 4, in which the fastening between the container part and the lid part on each wrapping cover comprises a resealable sealing means for the lid part of the wrapping cover.

8. The stack of absorbent articles according to claim 1, in which the stack is placed in an outer packing having an inside and an outside, and the first absorbent article is placed at one end of the stack and is arranged with the lid part of the first wrapping cover attached to the inside of the outer packing by a releasable attachment which is stronger than the attachment between the lid part and the container part on the wrapping cover of the first absorbent article.

* * * * *